United States Patent
Nishino et al.

(10) Patent No.: US 8,030,512 B2
(45) Date of Patent: Oct. 4, 2011

(54) POLYCYCLIC PENTAFLUOROSULFANYLBENZENE COMPOUND AND PROCESS FOR PRODUCING THE COMPOUND

(75) Inventors: Shigeyoshi Nishino, Yamaguchi (JP); Hidetaka Shima, Yamaguchi (JP); Hiroyuki Oda, Yamaguchi (JP); Yoji Omata, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 12/563,366

(22) Filed: Sep. 21, 2009

(65) Prior Publication Data

US 2010/0099909 A1   Apr. 22, 2010

(30) Foreign Application Priority Data

Oct. 20, 2008 (JP) .................. 2008-269986

(51) Int. Cl.
*C07C 69/76* (2006.01)
*C07C 41/00* (2006.01)
*C07C 43/02* (2006.01)
*C07C 43/20* (2006.01)

(52) U.S. Cl. ...................... 560/102; 568/631

(58) Field of Classification Search .................. None
See application file for complete search history.

(56) References Cited

U.S. PATENT DOCUMENTS

2006/0061699 A1* 3/2006 Kirsch et al. ............ 349/24

OTHER PUBLICATIONS

Silverman, The Organic Chemistry of Drug Design and Drug Action, 1992, Academic Press Inc. p. 15-22.*

* cited by examiner

*Primary Examiner* — Daniel Sullivan
*Assistant Examiner* — Jennifer C Sawyer
(74) *Attorney, Agent, or Firm* — Oblon, Spivak, McClelland, Maier & Neustadt, L.L.P.

(57) ABSTRACT

A polycyclic pentafluorosulfanylbenzene compound represented by the following general formula (1) and a process for producing the polycyclic pentafluorosulfanylbenzene compound which comprises reacting a specific pentafluorosulfanylbenzene compound with a specific boronic acid compound are provided. The polycyclic pentafluorosulfanylbenzene compound is a novel compound and can be produced by the process industrially advantageously.

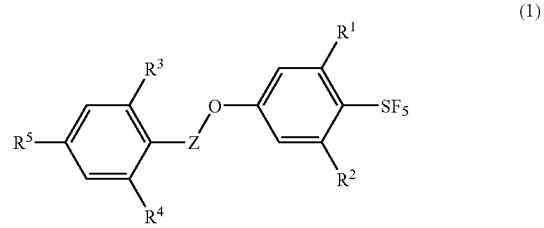

(1)

($R^1$ to $R^4$ each independently represent hydrogen atom or fluorine atom, $R^5$ represents a hydrocarbon group having at least two cyclic structures which may have substituents, and Z represents keto group, thioketo group, methylene group or difluoromethylene group.)

11 Claims, No Drawings

POLYCYCLIC PENTAFLUOROSULFANYLBENZENE COMPOUND AND PROCESS FOR PRODUCING THE COMPOUND

TECHNICAL FIELD

The present invention relates to a polycyclic pentafluorosulfanyl-benzene compound and a process for producing the compound

BACKGROUND ART

It is known that pentafluoro sulfur compounds having a specific structure, i.e., oxycarbonylpentafluorosulfanylbenzene compounds, are useful as the material for liquid crystals (for example, refer to Patent References 1 to 3).

Trifluorobenzene compounds having a polycyclic difluoromethyl ether and an ester bonding group are also known (for example, refer to Non-Patent Reference 1). However, a group of compounds obtained by substituting the trifluorobenzene in the above compounds with pentafluorosulfanylbenzene are not known, and properties of these compounds and processes for producing these compounds are not known, either.

[Patent Reference 1] Japanese Patent Application Laid-Open No. 2002-212163
[Patent Reference 2] International Patent Application Laid-Open No. 2005/047240
[Patent Reference 3] International Patent Application Laid-Open No. 2005/123749
[Non-Patent Reference 1] Journal of the SID 13/8, 2005

DISCLOSURE OF THE INVENTION

The present invention has an object of providing a novel polycyclic pentafluorosulfanylbenzene compound and a process for producing the compound industrially advantageously.

The present invention provides a novel polycyclic pentafluorosulfanyl-benzene compound described in [1] and a process for producing the compound described in [2].

[1] A polycyclic pentafluorosulfanylbenzene compound represented by following general formula (1):

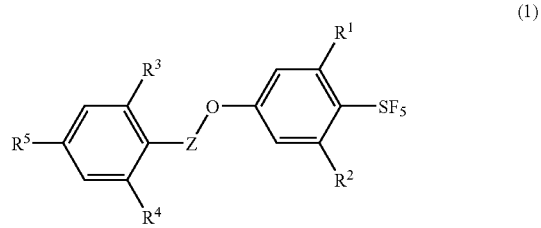

wherein $R^1$ to $R^4$ each independently represent hydrogen atom or fluorine atom, $R^5$ represents a hydrocarbon group having at least two cyclic structures which may have substituents, and Z represents keto group, thioketo group, methylene group or difluoromethylene group.

[2] A process for producing a polycyclic pentafluorosulfanyl-benzene compound represented by the above general formula (1) which comprises reacting a pentafluorosulfanylbenzene compound represented by general formula (3) with a boronic acid compound represented by general formula (4), general formulae (3) and (4) being:

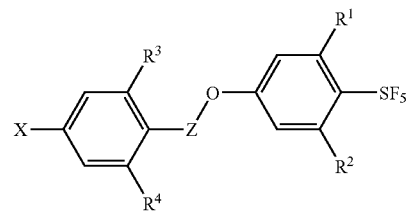

wherein $R^1$ to $R^4$ each independently represent hydrogen atom or fluorine atom, X represents a group which can be eliminated, and Z represents keto group, thioketo group, methylene group or difluoromethylene group; and $$R^5-BY_2 \qquad (4)$$

wherein $R^5$ represents a hydrocarbon group having at least two cyclic structures which may have substituents, Y represents hydroxyl group or an alkoxyl group having 1 to 10 carbon atoms, wherein two groups represented by Y may be same with or different from each other and, when two groups represented by Y are each an alkoxyl group, a cyclic structure formed by bonding two alkyl groups in the two alkoxyl groups to each other may be present.

THE EFFECT OF THE INVENTION

In accordance with the present invention, a novel polycyclic pentafluorosulfanylbenzene compound can be provided. This novel compound is useful in the fields of materials for liquid crystals and drugs.

In accordance with the process of the present invention, the polycyclic pentafluorosulfanylbenzene compound can be produced easily and industrially advantageously from easily available materials.

THE MOST PREFERRED EMBODIMENT TO CARRY OUT THE INVENTION (Polycyclic Pentafluorosulfanylbenzene Compound)

The polycyclic pentafluorosulfanylbenzene compound of the present invention is represented by the following general formula (1). In the following general formula (1), O and the group represented by Z may be bonded at the reversed positions.

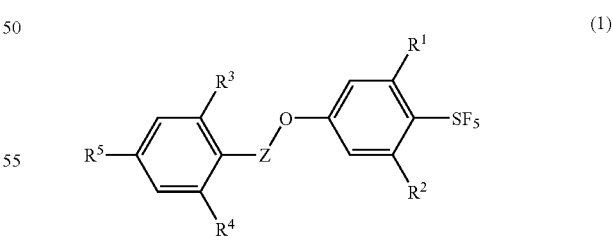

In general formula (1), $R^1$ to $R^4$ each independently represent hydrogen atom or fluorine atom and may represent the same atom or different atoms. It is preferable that at least one of $R^1$ and $R^2$ among $R^1$ to $R^4$ represents hydrogen atom, and it is more preferable that $R^1$ and $R^2$ both represent hydrogen atom. It is preferable that at least one of $R^3$ and $R^4$ among $R^1$ to $R^4$ represents fluorine atom, and it is more preferable that $R^3$ and $R^4$ both represent fluorine atom.

In general formula (1), hydrogen atom on the benzene ring may be substituted with a substituent. Examples of the substituent include alkyl groups having 1 to 20 carbon atoms and preferably 1 to 10 carbon atoms, cycloalkyl groups having 3 to 20 carbon atoms and preferably 3 to 10 carbon atoms, aralkyl groups having 7 to 20 carbon atoms and preferably 7 to 10 carbon atoms, aryl groups having 6 to 20 carbon atoms and preferably 6 to 10 carbon atoms, and heteroaryl groups having 2 to 20 carbon atoms and preferably 2 to 10 carbon atoms. Hydrogen atom on the benzene ring may be substituted with a substituent other than the substituents described above as the examples such as an electron attracting group and an electron donating group as long as the substituent does not affect the reactivity.

Examples of the substituent other than the substituents described above as the examples include substituents bonded through carbon atom, oxygen atom, nitrogen atom or sulfur atom and halogen atoms.

Specific examples of the above substituent include alkenyl groups, heterocyclic groups such as quinolyl groups, acyl group, carboxyl group, alkoxycarbonyl groups, aryloxycarbonyl groups, halogenated alkyl groups, cyano group, alkoxyl groups, aryloxyl groups, secondary amino groups, amido groups, heterocyclic amino groups, imino groups, thioalkoxyl groups and thioaryloxyl groups.

In general formula (1), Z represents keto group, thioketo group, methylene group or difluoromethylene group. From the standpoint of the properties of liquid crystals, keto group and difluoromethylene group are preferable.

$R^5$ represents a hydrocarbon group having at least three cyclic structures which may have substituents. In other words, in general formula (1), the group bonded to the group represented by Z at the left hand side on the paper is a hydrocarbon group having at least three cyclic structures.

It is preferable that $R^5$ represents a hydrocarbon group having at least one aromatic cyclic structure and at least one aromatic cyclic structure or alicyclic structure as the cyclic structures. Specifically, it is more preferable that $R^5$ represents a hydrocarbon group having biphenylyl group or a cycloalkylphenyl group, which may have substituents such as alkyl groups.

Preferable examples of the compound represented by general formula (1) include compounds represented by the following general formula (2). In the following general formula (2), O and the group represented by Z may be bonded at the reversed positions.

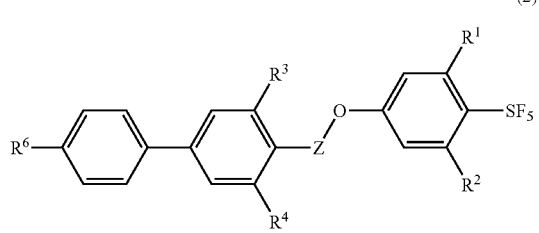

(2)

In general formula (2), $R^1$ to $R^4$ and Z are as described above, and $R^6$ represents a cycloalkyl group which may have alkyl groups having 1 to 10 carbon atoms or an aryl group which may have alkyl groups having 1 to 10 carbon atoms.

Examples of the alkyl group as the substituent include methyl group, ethyl group, propyl group, various types of butyl groups, various types of pentyl groups, various types of hexyl groups, various types of heptyl groups, various types of octyl groups, various types of nonyl groups and various types of decyl groups. Among these groups, alkyl groups having 2 to 9 carbon atoms are preferable, and alkyl groups having 3 to 8 carbon atoms are more preferable.

Examples of the cycloalkyl group described above (excluding alkyl groups as substituents) include cycloalkyl groups having 3 to 10 carbon atoms and preferably 5 to 8 carbon atoms such as cyclopropyl group, cyclobutyl group, cyclopentyl group, cyclohexyl group, cycloheptyl group and cyclooctyl group. Cyclohexyl group is more preferable among these cycloalkyl groups.

Examples of the aryl group described above (excluding alkyl groups as substituents) include aryl groups having 6 to 20 carbon atom and preferably 6 to 10 carbon atoms such as phenyl group, p-tolyl group, naphthyl group and anthryl group. Phenyl group is preferable among these aryl groups.

It is preferable that the compound represented by general formula (2) is a compound having a structure which is symmetric with respect to the virtual straight line connecting $R^6$ and Z on the paper in general formula (2).

Preferable examples of the compound represented by general formula (2) include compounds represented by the following general formulae (2-1), (2-2), (2-3) and (2-4).

In general formulae (2-1), (2-2), (2-3) and (2-4), $R^1$ to $R^4$ and Z are as described above, and $R^7$ represents an alkyl group having 1 to 10 carbon atoms, preferably 2 to 9 carbon atoms and more preferably 3 to 8 carbon atoms. In the following general formulae, O and a group represented by Z may be bonded at the reversed positions.

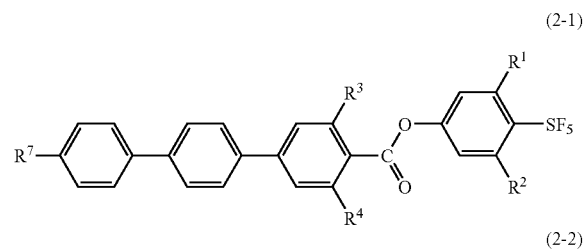

(2-1)

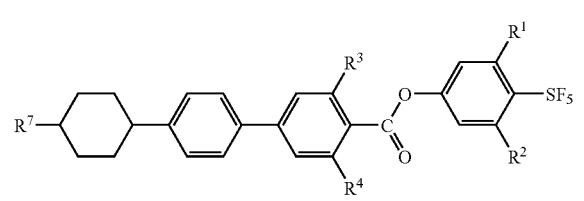

(2-2)

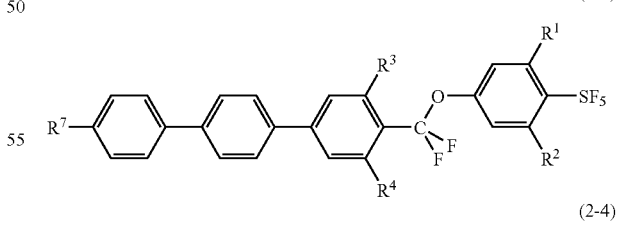

(2-3)

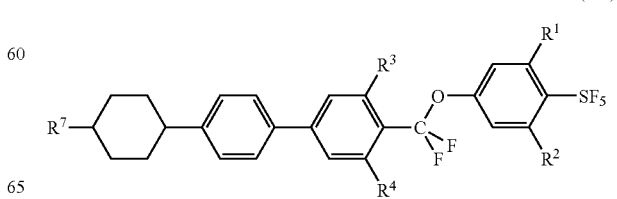

(2-4)

(Process for Producing a Polycyclic Pentafluorosulfanylbenzene Compound)

The process for producing a polycyclic pentafluorosulfanylbenzene compound of the present invention is characterized in that a pentafluorosulfanylbenzene compound is reacted with a boronic acid compound.

(Pentafluorosulfanylbenzene Compound)

The pentafluorosulfanylbenzene compound used as the raw material in the process of the present invention is represented by the following general formula (3). In the following general formula (3), O and the group represented by Z may be bonded at the reversed positions.

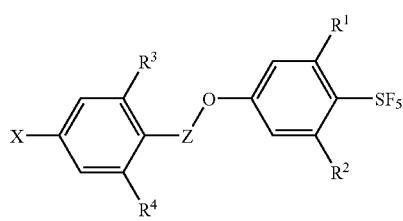

(3)

In general formula (3), $R^1$ to $R^4$ and Z are as described above, and X represents a group which can be eliminated.

"The group which can be eliminated", which is represented by X, is not particularly limited as long as the group can be substantially eliminated. Examples of the group represented by X include halogen atoms such as chlorine atom, bromine atom and iodine atom, alkyl-sulfonyloxy groups such as methanesulfonyloxy group, arylsulfonyloxy groups such as benzenesulfonyloxy group and p-toluenesulfonyloxy group, organic sulfonyloxy groups such as trifluoromethanesulfonyloxy group, oxycarbonylalkyl groups such as —OCOR groups and trialkylsilyl groups such as —SiR$_3$ groups (R representing an alkyl group having 1 to 10 carbon atoms).

Among these groups, halogen atoms are preferable, chlorine atom, bromine atom and iodine atom are more preferable, and bromine atom and iodine atom are most preferable as the group represented by X.

X may represent a group which is other than those described above and is eliminated in a equivalent manner to halogen atoms, such as a halogenocarbonyl group, a halogenosulfonyl group and diazo group (for example, refer to E. Negishi, "Handbook of Organopalladium Chemistry for Organic Synthesis", Volume 1, Wiley Interscience, page 1133, published in 2002).

(Boronic Acid Compound)

The boronic acid compound used in the process of the present invention is represented by the following general formula (4):

$$R^5\text{—}BY_2 \quad (4)$$

In general formula (4), $R^5$ represents a hydrocarbon group having at least two cyclic structures which may have substituents as described above, Y represents hydroxyl group or an alkoxyl group having 1 to 10 carbon atoms and preferably 1 to 8 carbon atoms, wherein two groups represented by Y may be the same with or different from each other and, when two groups represented by Y are each an alkoxyl group, a cyclic structure formed by bonding two alkyl groups in the two alkoxyl groups to each other may be present.

Examples of the boronic acid compound described above include boronic acids represented by general formula (4-1), anhydrides of trimers of the boronic acids and equivalent mixtures thereof represented by general formula (4-2) and boronic acid esters represented by general formula (4-3), which are shown in the following. In the following general formulae, $R^5$ is as described above.

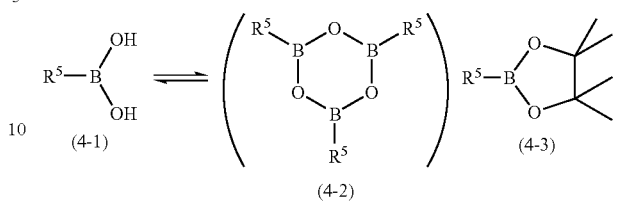

Among the above boronic acid compounds, boronic acid esters represented by general formula (4-3) are preferable and, specifically, compounds represented by the following general formulae (4-4) and (4-5) are more preferable. In the following general formulae (4-4) and (4-5), $R^7$ is as described above. An organic trifluoroboronic acid salt such as $R^5$—$BF_3K$ may be used in place of the boronic acid compound.

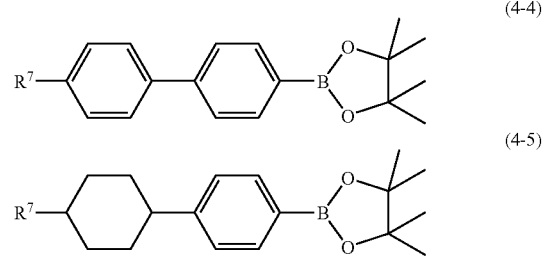

It is preferable that the amount of the boronic acid compound used in the process of the present invention is 0.5 to 10 moles, more preferably 0.6 to 5 moles and most preferably 0.7 to 2 moles based on 1 mole of the pentafluorosulfanylbenzene compound represented by general formula (3).

It is preferable that the process of the present invention is conducted in the presence of a solvent. The solvent is not particularly limited as long as the reaction is not adversely affected. Examples of the solvent include water, alcohols, amines, ketones, amides, ureas, sulfoxides, sulfones, nitriles, ethers, aromatic hydrocarbons, halogenated aromatic hydrocarbon and halogenated aliphatic hydrocarbons.

Examples of the alcohol include methanol, ethanol, isopropyl alcohol and t-butyl alcohol. Examples of the amine include primary amines such as ethylamine, aniline and benzylamine, secondary amines such as dimethylamine, diethylamine, diisopropylamine, methylethylamine, and diphenylamine, tertiary amines such as trimethyl-amine, triethylamine, tributylamine and diisopropylethylamine, and heterocyclic amines such as pyrrolidine pyridine and quinoline.

Examples of the ketone include acetone, methyl ethyl ketone and methyl isobutyl ketone. Examples of the amide include N,N-dimethyl-formamide, N,N-dimethylacetamide and N-methylpyrrolidone. Examples of the urea include 1,3-dimethyl-2-imidazolidinone and 1,3-dimethylimidazolidin-2,4-dione.

Examples of the sulfoxide include dimethyl sulfoxide. Examples of the sulfone include sulfolane. Examples of the nitrile include acetonitrile and propionitrile. Examples of the ether include diethyl ether, diisopropyl ether, tetrahydrofuran, dimethoxyethane and dioxane. Examples of the aromatic hydrocarbon include benzene, toluene and xylene. Examples of the halogenated aromatic hydrocarbon include chlorobenzene and dichlorobenzene. Examples of the halogenated aliphatic hydrocarbon include dichloromethane and chloroform.

Among these solvents, water, alcohols, ketones, amides, ureas, sulfoxides, ethers, aromatic hydrocarbons and halogenated aliphatic hydrocarbons are preferable, alcohols, amides, ureas, ethers and aromatic hydrocarbons are more preferable, and ethers and aromatic hydrocarbons are most preferable. The solvent may be used singly or in combination of two or more.

It is preferable that the solvent is used in an amount of 1 to 100 ml, more preferably 2 to 50 ml and most preferably 3 to 30 ml based on 1 g of the pentafluorosulfanylbenzene compound represented by general formula (3).

It is preferable that the process of the present invention is conducted in the presence of a base and/or a metal compound.

Examples of the base which can be used include alkali metal hydroxides, alkali metal carbonates, alkali metal hydrogencarbonates, phosphoric acid salts, alkali metal alkoxides, alkali metal hydrides, alkaline earth metal hydrides and amines.

Examples of the alkali metal hydroxide include sodium hydroxide and potassium hydroxide. Examples of the alkali metal carbonate include sodium carbonate and potassium carbonate. Examples of the alkali metal hydrogencarbonate include sodium hydrogencarbonate and potassium hydrogencarbonate. Examples of the phosphoric acid salt include trisodium phosphate, tripotassium phosphate, dipotassium hydrogenphosphate and potassium dihydrogenphosphate.

Examples of the alkali metal alkoxide include sodium methoxide, potassium methoxide, sodium ethoxide, potassium ethoxide, sodium t-butoxide and potassium t-butoxide. Examples of the alkali metal hydride and the alkaline earth metal hydride include lithium hydride, sodium hydride, potassium hydride and calcium hydride.

Examples of the amine include primary amines such as ethylamine, propylamine, butylamine, aniline and benzylamine, secondary amines such as dimethylamine, diethylamine, dipropylamine, diisopropylamine, dibutylamine, methylethylamine, methylpropylamine and diphenylamine, tertiary amines such as trimethylamine, triethylamine, tributylamine and diisopropylethylamine, and heterocyclic amines such as pyrrolidine, piperidine and pyridine.

Among these bases, alkali metal carbonates, phosphoric acid salts and amines are preferable and, specifically, potassium carbonate, tripotassium phosphate and triethylamine are more preferable. The base may be used singly or as a mixture of two or more and may be used as an aqueous solution or a solution in an organic solvent.

It is preferable that the base described above is used in an amount of 0.5 to 10.0 moles, more preferably 0.8 to 5.0 moles and most preferably 1.0 to 3.0 mole based on the amount of the pentafluorosulfanylbenzene compound represented by general formula (3).

Examples of the metal compound which can be used include acid salts of palladium, chlorides of palladium, complex compounds of palladium, compounds supporting palladium, nickel compounds, cobalt compounds and rhodium compounds (for example, refer to "JIKKEN KAGAKU KOZA (Experimental Chemistry Series)", edited by Japanese Chemical Society, edition, pages 164 and 165).

Examples of the acid salt of palladium include palladium acetate, bis(acetate)bis(triphenylphosphine)palladium, dichlorobis(triphenylphosphine)palladium, bis(acetonitrile)dichloropalladium and bis(benzonitrile)dichloropalladium. Examples of the chloride of palladium include palladium chloride. Examples of the complex compound of palladium include tetrakis(triphenylphosphine)palladium, tris(dibenzylideneacetone)dipalladium and heterocyclic carbene palladium complex compounds having nitrogen such as dichloro{1,3-bis(2,6-diisopropylphenypimidazol-2-ylidene}(3-chloropyridyl)palladium, allyl-chloro{1,3-bis(2,6-diisopropylphenyl)imidazol-2-ylidene}palladium, 1,3-bis-(2,6-diisopropylphenyl)imidazol-2-ylidene(1,4-naphthoquinone)palladium dimer and 1,3-bis(2,4,6-trimethylphenyl)imidazol-2-ylidene-(1,4-naphthoquinone) palladium dimer. Examples of the compound supporting palladium include palladium/carbon, palladium/barium sulfate and palladium-platinum/carbon.

Examples of the nickel compound include bis(cyclopentadienyl)-nickel and dichlorobis(triphenylphosphine)nickel. Examples of the cobalt compound include dichloro(diphenylphosphinohexane)cobalt. Examples of the rhodium compound include chloro(1,5-cyclooctadiene)rhodium dimer.

Among these metal compounds, palladium compounds are preferable, and tetrakis(triphenylphosphine)palladium is more preferable. The metal compound may be used singly or as a mixture of two or more.

For example, dichlorobis(triphenylphosphine)palladium may be used in the form available as a commercial product or may be prepared from palladium chloride and triphenylphosphine in the reaction system with or without isolation.

It is preferable that the metal compound is used in an amount of 0.1 to 100% by mole, more preferably 0.1 to 50% by mole and most preferably 0.1 to 20% by mole based on 1 mole of the pentafluorosulfanyl-benzene compound represented by general formula (3).

In the process of the present invention, a phosphine ligand or a phase transfer catalyst may be present to control the reactivity (for example, refer to Tetrahedron, 52, 10113 (1996)).

Examples of the phosphine ligand which can be used include trialkylphosphines such as tri-n-butylphosphine, tri-t-butylphosphine and tricyclohexylphosphine, triarylphosphines such as triphenylphosphine and tri-o-tolylphosphine, diphosphines such as 1,4-bis(diphenyl-phosphino)butane and 1,1'-bis(diphenylphosphino)ferrocene, and dialkylbiarylphosphines such as 2-dicyclohexylphosphino-2',6'-dimethoxybiphenyl, 2-dicyclohexylphosphino-2',4',6'-triisopropylbiphenyl and 1,2,3,4,5-pentaphenyl-1'-(di-tertiarybutyl-phosphino)ferrocene. Among these phosphine ligands, trialkylphosphines are preferable, and tri-t-butylphosphine is more preferable.

Examples of the phase transfer catalyst which can be used include tetra-n-methylammonium chloride, tetra-n-butylammonium fluoride, tetra-n-butylammonium chloride, tetra-n-butylammonium bromide, tetra-n-butylammonium tribromide, tetra-n-butylammonium iodide, tetra-n-butylammonium acetate, tetra-n-butylammonium hydrogensulfate, tetra-n-butylammonium nitrate, tetra-n-butylammonium methane-sulfonate, tetra-n-butylammonium trifluoromethanesulfonate, tetra-n-butylammonium cyanide, hydroxy-tetra-n-butylammonium hydrate, tetra-n-butylammonium hexafluorophosphate, tetra-n-butylammonium tetrafluoroborate and tetra-n-butylammonium perchlorate.

The phosphine ligand and the phase transfer catalyst may be used singly or as a mixture of two or more. The phosphine ligand and the phase transfer catalyst may be each a hydrate. The phosphine ligand and the phase transfer catalyst may be used in combination.

It is preferable that the phosphine ligand or the phase transfer catalyst is used in an amount of 0 to 100 moles, more preferably 0 to 50 moles and most preferably 0 to 10 moles based on 1 mole of the palladium atom when the metal compound and, in particular, the palladium compound is used.

The process of the present invention is conducted, for example, by mixing the pentafluorosulfanylbenzene compound described above, the boronic acid compound described above, the solvent, the metal oxide and the base with stirring to allow the reaction to proceed. It is preferable that the reaction temperature is 0 to 200° C., more preferably 20 to 150° C. and most preferably 60 to 120° C. The reaction pressure is not particularly limited. In general, the reaction is conducted under the atmospheric pressure or an added pressure.

The polycyclic pentafluorosulfanylbenzene compound can be obtained in accordance with the process of the present invention. The object compound can be isolated and purified by a conventional process such as neutralization, extraction, filtration, concentration, distillation, recrystallization, crystallization, sublimation and the column chromatography after the reaction is completed.

As the process for producing the polycyclic pentafluorosulfanylbenzene compound of the present invention other than the process described above, the polycyclic pentafluorosulfanylbenzene compound can be synthesized by reacting compounds having structures obtained by exchanging the group which can be eliminated (X) in the pentafluorosulfanylbenzene compound and boryl group ($-BY_2$) in the boronic acid compound. For example, the polycyclic pentafluorosulfanylbenzene compound can be synthesized by reacting a pentafluorosulfanylbenzene compound having $BY_2$ group with $R_5X$.

EXAMPLES

The present invention will be described more specifically with reference to examples in the following. However, the present invention is not limited to the examples.

Example 1

Synthesis of 3,5-difluoro-4'-(4-propylcyclohexyl) biphenyl-4-carbonyloxypentafluorosulfanylbenzene Into a vessel having an inner volume of 30 ml which was equipped with a stirring apparatus, a thermometer and a reflux condenser, 0.439 g (1.00 mmol) of 1-bromo-3,5-difluoro-4-carbonyloxypentafluorosulfanyl-benzene, 0.535 g (1.50 mmol) of 4,4,5,5-tetramethyl-2-[4-(4-pentyl-cylohexyl)phenyl)]-[1,3,2]-dioxaborane, 0.070 g (0.060 mmol) of tetrakis-(triphenylphosphine)palladium, 0.425 g (2.00 mmol) of tripotassium phosphate in the powder form and 5 ml of 1,4-dioxane were placed, and the reaction was allowed to proceed at 100° C. for 7.5 hours with stirring.

After the reaction was completed, the reaction mixture was filtered, and the filtrate was concentrated under a reduced pressure. Then, the resulting residue was purified by the normal phase silica gel column chromatography (eluent:hexane and hexane/ethyl acetate=95/5) and the reversed phase silica gel column chromatography (ODSC-18; eluent: acetonitrile/water=95/5→100/0 (the ratio of the amounts by volume)), and 0.290 g (isolated yield: 49%) of 3,5-difluoro-4'-(4-propylcyclohexyl)biphenyl-4-carbonyloxypentafluorosulfanylbenzene was obtained as a white solid. The reaction scheme is shown in the following:

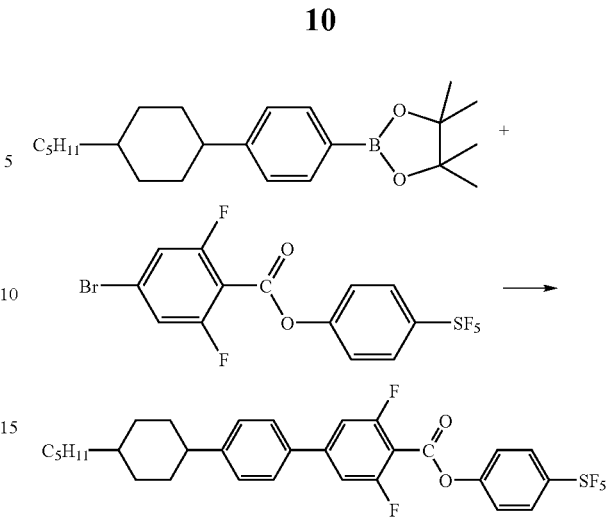

The obtained compound is a novel compound as exhibited by the following physical properties:

$^1$H-NMR (CDCl$_3$, δ (ppm)): 0.90 (3H, t, J=7.0 Hz), 1.02~1.51 (13H, m), 1.88~1.94 (4H, m), 2.49~2.60 (1H, m), 7.23~7.41 (6H, m), 7.51~7.54 (2H, m), 7.82~7.88 (2H, m)

CI-MS: 589 (M+1)

Example 2

Synthesis of 4-{3",5"-difluoro-4-heptyl-[1,1';4',1"]-terphenyl-4"-yloxycarbonyl}pentafluorosulfanylbenzene Into a vessel having an inner volume of 30 ml which was equipped with a stirring apparatus, a thermometer and a reflux condenser, 0.439 g (1.00 mmol) of 1-bromo-3,5-difluoro-4-carbonyloxypentafluorosulfanyl-benzene, 0.568 g (1.50 mmol) of 4-(4-n-heptylbiphenyl)boronic acid pinacol ester, 0.070 g (0.061 mmol) of tetrakis(triphenylphosphine)-palladium, 0.425 g (2.00 mmol) of tripotassium phosphate in the powder form and 5 ml of 1,4-dioxane were placed, and the reaction was allowed to proceed at 100° C. for 6 hours with stirring. After the reaction was completed, the reaction mixture was filtered, and the filtrate was concentrated under a reduced pressure. Then, the resulting residue was purified by the flush column chromatography (eluent:hexane), and 0.04 g (isolated yield: 7%) of 4-{3",5"-difluoro-4-heptyl-[1,1';4',1"]-terphenyl-4"-yloxycarbonyl}pentafluorosulfanyl-benzene was obtained as a white solid. The reaction scheme is shown in the following:

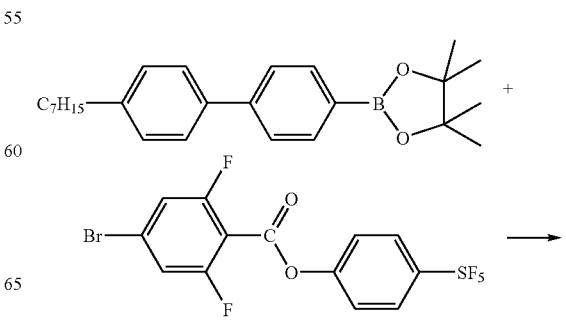

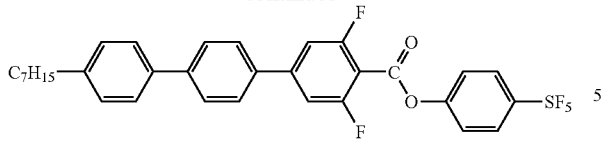

The obtained compound is a novel compound as exhibited by the following physical properties:

$^1$H-NMR (CDCl$_3$, δ (ppm)): 0.89 (3H, t, J=6.8 Hz), 1.26~1.36 (8H, m), 1.61~1.69 (2H, m), 2.67 (2H, m), 7.28~7.42 (6H, m), 7.55~7.88 (8H, m)

CI-MS: 610 (M)

Example 3

Synthesis of 4-{[3,5-difluoro-4'-(4-propylcyclohexyl)biphenyl-4-yl] difluoromethoxy}pentafluorosulfanylbenzene Into a vessel having an inner volume of 30 ml which was equipped with a stirring apparatus, a thermometer and a reflux condenser, 0.460 g (1.00 mmol) of 4-[(4-bromo-2,6-difluorophenyl)difluoromethoxy]pentafluorosulfanylbenzene, 0.330 g (1.00 mmol) of 4,4,5,5-tetramethyl-2-[4-(4-propylcylohexyl)phenyl)]-[1,3,2]-dioxaborane, 0.070 g (0.060 mmol) of tetrakis(triphenylphosphine)palladium, 0.428 g (2.00 mmol) of tripotassium phosphate in the powder form and 5 ml of 1,4-dioxane were placed, and the reaction was allowed to proceed at 100° C. for 4 hours with stirring. After the reaction was completed, the reaction mixture was filtered, and the filtrate was concentrated under a reduced pressure. Then, the resulting residue was purified by the normal phase silica gel column chromatography (eluent: hexane), and 0.250 g (isolated yield: 43%) of 4-{[3,5-difluoro-4'-(4-propylcyclohexyl)biphenyl-4-yl] difluoromethoxy}pentafluorosulfanylbenzene was obtained as a white solid. The reaction scheme is shown in the following:

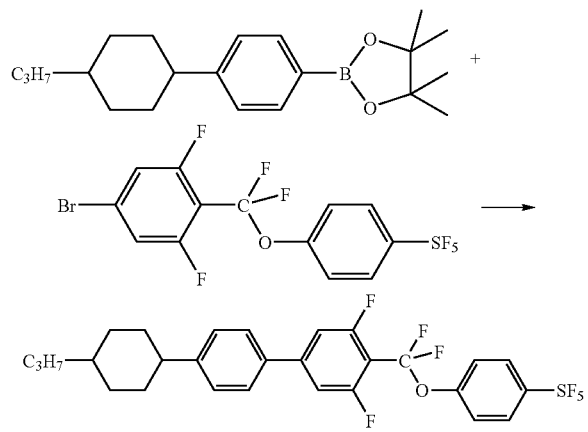

The obtained compound is a novel compound as exhibited by the following physical properties:

$^1$H-NMR (CDCl$_3$, δ (ppm)): 0.91 (3H, t, J=7.1 Hz), 1.05~1.51 (9H, m), 1.91~1.94 (4H, m), 2.49~2.57 (1H, m), 7.19~7.39 (6H, m), 7.48~7.51 (2H, m), 7.75~7.80 (2H, m)

CI-MS: 582 (M)

Example 4

Synthesis of 4-{[3,5-difluoro-4'-(4-n-pentylcyclohexyl)-biphenyl-4-yl] difluoromethoxy}pentafluorosulfanylbenzene Into a vessel having an inner volume of 30 ml which was equipped with a stirring apparatus, a thermometer and a reflux condenser, 0.460 g (1.00 mmol) of 4-[(4-bromo-2,6-difluorophenyl)difluoromethoxy]pentafluorosulfanylbenzene, 0.411 g (1.15 mmol) of 4-(4-n-pentylcyclohexyl)-phenylboronic acid pinacol ester, 0.070 g (0.061 mmol) of tetrakis-(triphenylphosphine)palladium, 0.425 g (2.02 mmol) of tripotassium phosphate in the powder form and 5 ml of 1,4-dioxane were placed, and the reaction was allowed to proceed at 100° C. for 12 hours with stirring. After the reaction was completed, the reaction mixture was filtered, and the filtrate was concentrated under a reduced pressure. Then, the resulting residue was purified by the flush column chromatography (eluent: hexane), and 0.36 g (isolated yield: 59%) of 4-{[3,5-difluoro-4'-(4-n-pentylcyclohexyl)-biphenyl-4-yl] difluoromethoxy}pentafluorosulfanylbenzene was obtained as a white solid. The reaction scheme is shown in the following:

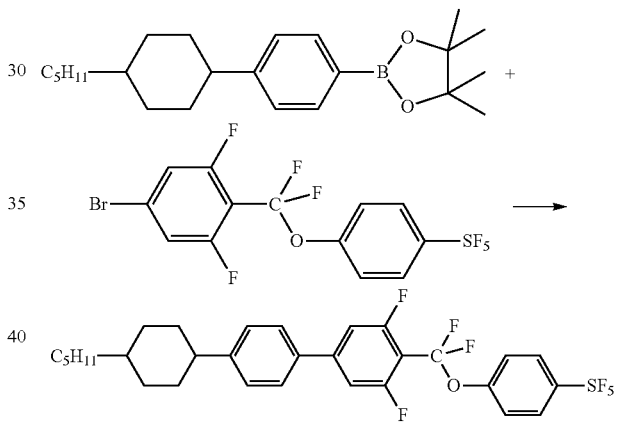

The obtained compound is a novel compound as exhibited by the following physical properties:

$^1$H-NMR (CDCl$_3$, δ (ppm)): 0.90 (3H, t, J=7.0 Hz), 1.05~1.51 (13H, m), 1.89~1.90 (4H, m), 2.49~2.57 (1H, m), 7.19~7.39 (6H, m), 7.48~7.51 (2H, m), 7.75~7.80 (2H, m)

CI-MS: 382 (M−229)

Example 5

Synthesis of 4-[(3",5"-difluoro-4-heptyl-[1,1';4',1"]-terphenyl-4"-yl)difluoromethoxy]pentafluorosulfanylbenzene Into a vessel having an inner volume of 30 ml which was equipped with a stirring apparatus, a thermometer and a reflux condenser, 0.461 g (1.00 mmol) of 4-[(4-bromo-2,6-difluorophenyl)difluoromethoxy]pentafluorosulfanylbenzene, 0.568 g (1.5 mmol) of 4-(4-n-heptylbiphenyl)-boronic acid pinacol ester, 0.070 g (0.061 mmol) of tetrakis-(triphenylphosphine)palladium, 0.425 g (2.00 mmol) of tripotassium phosphate in the powder form and 5 ml of 1,4-dioxane were placed, and the reaction was allowed to proceed at 100°

C. for 12 hours with stirring. After the reaction was completed, the reaction mixture was filtered, and the filtrate was concentrated under a reduced pressure. Then, the resulting residue was purified by the flush column chromatography (eluent: hexane), and 0.160 g (isolated yield: 25%) of 4-[(3", 5"-difluoro-4-heptyl-[1,1';4',1"]-terphenyl-4"-yl)difluoromethoxy]pentafluorosulfanylbenzene was obtained as a white solid. The reaction scheme is shown in the following:

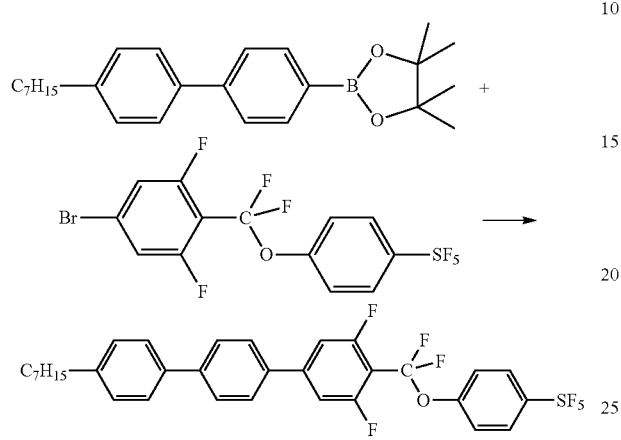

The obtained compound is a novel compound as exhibited by the following physical properties:

$^1$H-NMR (CDCl$_3$, δ (ppm)): 0.89 (3H, t, J=7.0 Hz), 1.26~1.34 (8H, m), 1.64~1.69 (2H, m), 2.66 (2H, m), 7.25~7.40 (6H, m), 7.53~7.80 (8H, m)
CI-MS: 329 (M−303)

INDUSTRIAL APPLICABILITY

The pentafluorosulfanylbenzene compound obtained by the process of the present invention is useful as an intermediate compound of synthesis in the fields of materials for liquid crystals and drugs.

What is claimed is:

1. A polycyclic pentafluorosulfanylbenzene compound represented by formula (2):

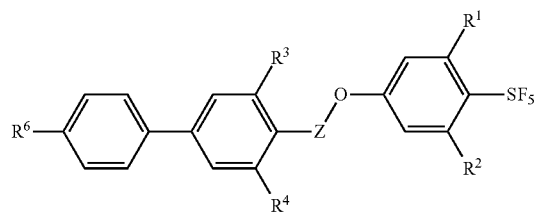

(2)

wherein $R^1$ to $R^4$ each independently represent hydrogen atom or fluorine atom, Z represents a keto group, a thioketo group, a methylene group or a difluoromethylene group, and $R^6$ represents an aryl group which itself may optionally be substituted with alkyl groups having 1 to 10 carbon atoms.

2. The polycyclic pentafluorosulfanylbenzene compound according to claim 1, wherein Z represents a keto group.

3. The polycyclic pentafluorosulfanylbenzene compound according to claim 1, wherein Z represents a thioketo group.

4. The polycyclic pentafluorosulfanylbenzene compound according to claim 1, wherein Z represents a methylene group.

5. The polycyclic pentafluorosulfanylbenzene compound according to claim 1, wherein Z represents a difluoromethylene group.

6. The polycyclic pentafluorosulfanylbenzene compound according to claim 1, wherein the compound is represented by formula (2-1):

(2-1)

where $R^7$ represents an alkyl group having 1 to 10 carbon atoms.

7. The polycyclic pentafluorosulfanylbenzene compound according to claim 1, wherein the compound is represented by formula (2-3):

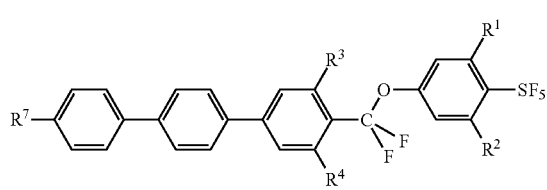

(2-1)

where $R^7$ represents an alkyl group having 1 to 10 carbon atoms.

8. The polycyclic pentafluorosulfanylbenzene compound according to claim 1, wherein the compound is represented by the following formula:

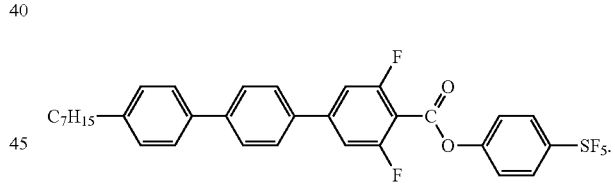

9. The polycyclic pentafluorosulfanylbenzene compound according to claim 1, wherein the compound is represented by the following formula:

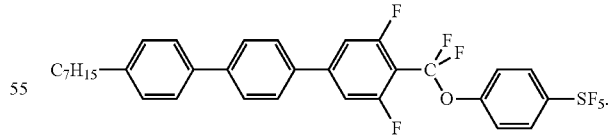

10. The polycyclic pentafluorosulfanylbenzene compound according to claim 1, wherein the aryl group is selected from the group consisting of a phenyl group, a p-tolyl group, a naphthyl group and an anthryl group.

11. The polycyclic pentafluorosulfanylbenzene compound according to claim 1, wherein the aryl group is a phenyl group.

* * * * *